United States Patent [19]
Schäfer et al.

[11] Patent Number: 5,700,805
[45] Date of Patent: Dec. 23, 1997

[54] SUBSTITUTED 1-AMINO-3-PHENYLURACILS

[75] Inventors: Peter Schäfer, Ottersheim; Ralf Klintz, Gruenstadt; Gerhard Hamprecht, Weinheim; Elisabeth Heistracher, Ludwigshafen; Karl-Otto Westphalen, Speyer; Matthias Gerber, Limburgerhof; Helmut Walter, Obrigheim, all of Germany

[73] Assignee: BASF Aktiengesellschaft, Ludwigshafen, Germany

[21] Appl. No.: 596,215
[22] PCT Filed: Aug. 25, 1994
[86] PCT No.: PCT/EP94/02821
  § 371 Date: Feb. 15, 1996
  § 102(e) Date: Feb. 15, 1996
[87] PCT Pub. No.: WO95/06641
  PCT Pub. Date: Mar. 9, 1995

[30] Foreign Application Priority Data

Sep. 2, 1993 [DE] Germany ............ 43 29 537.1

[51] Int. Cl.$^6$ .................. A01N 43/54; C07D 239/54; C07D 239/56
[52] U.S. Cl. .................. 514/269; 514/274; 544/298; 544/309; 544/311; 544/312
[58] Field of Search ............ 544/309, 312, 544/298, 311; 514/275, 269

[56] References Cited

U.S. PATENT DOCUMENTS 4,859,229  8/1989  Wenger et al. ............... 71/92

FOREIGN PATENT DOCUMENTS

| 255 047 | 2/1988 | European Pat. Off. |
| 408 382 | 1/1991 | European Pat. Off. |
| 420 194 | 4/1991 | European Pat. Off. |
| 517 181 | 12/1992 | European Pat. Off. |
| WO/91/11442 | 2/1990 | WIPO |
| WO/93/06090 | 9/1991 | WIPO |
| WO 94/04511 | 3/1994 | WIPO |

OTHER PUBLICATIONS

Heterocycles, vol. 119, 1993, p. 939, 160310e, Oct. 11, 1993.
Heterocycles, vol. 119, 1993, p. 1101, 95542r, Aug. 30, 1993.

Primary Examiner—Mukund J. Shah
Assistant Examiner—Sabiha Qazi
Attorney, Agent, or Firm—Keil & Weinkauf

[57] ABSTRACT

Substituted 1-amino-3-phenyluracils I

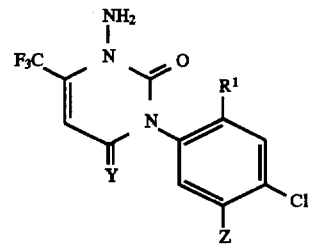

where the variables have the following meanings:

$R^1$=H, F, Cl; Y=O, S; Z=—CH=N—OH, —CH=N—O—(alkyl),
—CH=N—O—(alkylene)—O—(alkyl), —CH=N—O—CH$_2$—COOH,
—CH=N—O—CH(alkyl)—COOH, —CH=N—O—CH$_2$—CO—O—(alkyl),
—CH=N—O—CH(alkyl)—CO—O—(alkyl), —CH=N—O—CH$_2$—CO—O=O—(alkylene)—O—(alkyl),
—CH=N—O—CH(alkyl)—CO—O—(alkylene)—O—(alkyl), —CH=CH—CO—O—(alkyl), —CH=CH—CO—O—(alkylene)—O—(alkyl),
—CH=C(Cl)—CO—O—(alkyl), —CH=C(Br)—CO—O—(alkyl),
—CH=C(Cl)—CO—O—(alkylene)—O—(alkyl),
—CH=C(Br)—CO—O—(alkylene)—O—(alkyl),
—CH=C(CH$_3$)—CO—O—(alkyl),
—CH=C(CH$_3$)—CO—O—(alkylene)—O—(alkyl),
—CH[X$^1$-(alkyl)] [X$^2$-(alkyl)] or a radical

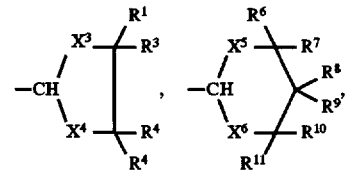

$X^1$-$X^6$=O, S; $R^2$-$R^{11}$=H, alkyl, vinyl, alkoxycarbonyl are described.

Use: herbicides; desiccation/defoliation of plants.

6 Claims, No Drawings

SUBSTITUTED 1-AMINO-3-PHENYLURACILS

This application is a continuation of 371 of PCT/EP94/02821, published as WO95/06641 Mar. 9, 1995.

The present invention relates to 1-amino-3-phenyluracils of the formula I

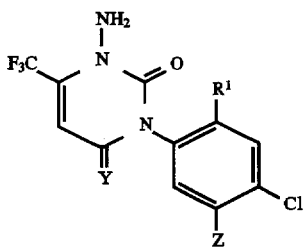

where the variables have the following meanings:
$R^1$ is hydrogen, fluorine or chlorine;
Y is oxygen or sulfur;
Z is —CH=N—OH, —CH=N—O—($C_1$-$C_6$-alkyl),
—CH=N—O—($C_1$-$C_6$-alkylene)—O—($C_1$-$C_6$-alkyl),
—CH=N—O—$CH_2$—COOH, —CH=N—O—CH ($C_1$-$C_6$-alkyl)—COOH,
—CH=N—O—$CH_2$—CO—O—($C_1$-$C_6$-alkyl),
—CH=N—O—CH ($C_1$-$C_6$-alkyl)—CO—O—($C_1$-$C_6$-alkyl),
—CH=N—O—$CH_2$—CO—O—($C_1$-$C_6$-alkylene)—O—($C_1$-$C_6$-alkyl),
—CH=N—O—CH($C_1$-$C_6$-alkyl)—CO—O—($C_1$-$C_6$-alkylene)—O—($C_1$-$C_6$-alkyl)
—CH=CH—CO—O—($C_1$-$C_6$-alkyl),
—CH=CH—CO—O—($C_1$-$C_6$-alkylene)—O—($C_1$-$C_6$-alkyl),
—CH=C(Cl)—CO—O—($C_1$-$C_6$-alkyl),
—CH=C(Br)—CO—O—($C_1$-$C_6$-alkyl),
—CH=C(Cl)—CO—O—($C_1$-$C_6$-alkylene )—O—($C_1$-$C_6$-alkyl),
—CH=C(Br)—CO—O—($C_1$-$C_6$-alkylene )—O—($C_1$-$C_6$-alkyl) ,
—CH=C($CH_3$)—CO—O—($C_1$-$C_6$-alkyl),
—CH=C($CH_3$)—CO—O—($C_1$-$C_6$-alkylene)—O—($C_1$-$C_6$-alkyl),
—CH[$X^1$-($C_1$-$C_6$-alkyl)] [$X^2$-($C_1$-$C_6$-alkyl)] or a radical

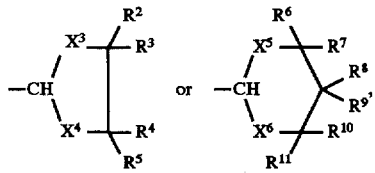

where
$X^1$–$X^6$ in each case are oxygen or sulfur and
$R^2$–$R^{11}$ in each case are hydrogen, $C_1$-$C_4$-alkyl, vinyl or $C_1$-$C_4$-alkoxycarbonyl.

In addition, the invention relates to herbicidal and desiccant and/or defoliant compositions which contain these compounds as active substances. The invention additionally relates to processes for the preparation of the compounds I and of herbicidal or desiccant and/or defoliant compositions, processes for the control of undesired plant growth and processes for the desiccation and/or defoliation of plants, in particular of cotton, using the compounds I.

1-Amino-3-phenyluracils of the compound I type are disclosed eg. in EP-A 420 194, EP-A 476 697 and EP-A 517 181.

A multiplicity of herbicidal 3-phenyluracils are disclosed in WO 93/06090. The particularly advantageous properties of the 1-amino-3-phenyluracils, however, cannot be inferred from this publication.

Since the known compounds are not always completely satisfactory with respect to their herbicidal or desiccant/defoliant action, the object of the present invention were novel, in particular herbicidal, compounds with which undesired plants can be specifically controlled better than hitherto.

The substituted 1-amino-3-phenyluracils of the formula I have therefore been found. Herbicidal compositions have further been found which contain the compounds I and have a very good herbicidal action.

The compounds I according to the invention are suitable in addition for the defoliation and desiccation of parts of plants for eg. cotton, potato, rape, sunflower, soybean or field beans.

The substituents $C_1$-$C_4$-alkyl, $C_1$-$C_6$-alkyl and $C_1$-$C_4$-alkoxycarbonyl in the radicals Z and $R^2$–$R^{11}$ are collective terms for individual lists of the separate group members. Specifically, they have the following meanings:

$C_1$-$C_4$-alkyl: methyl, ethyl, n-propyl, 1-methylethyl, n-butyl, 1-methylpropyl, 2-methylpropyl and 1,1-dimethylethyl, preferably methyl and ethyl;

$C_1$-$C_6$-alkyl: inter alia $C_1$-$C_4$-alkyl as mentioned above, and also n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably methyl and ethyl;

$C_1$-$C_4$-alkoxycarbonyl: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl, preferably methoxycarbonyl and ethoxycarbonyl.

$C_1$-$C_6$-Alkylene is understood as meaning, inter alia, methylene, 1,1-ethylene, 1,2-ethylene, 1,1-propylene, 1,2-propylene, 1,3-propylene, 2,2-propylene, 1,1-butylene, 1,2-butylene, 1,3-butylene, 1,4-butylene, 2,2-butylene, 2,3-butylene, 2-methyl-1,1-propylene, 2-methyl-1,2-propylene, 2-methyl-1,3-propylene, 1,1-pentylene, 1,2-pentylene, 1,3-pentylene, 1,4-pentylene, 1,5-pentylene, 2,2-pentylene, 2,3-pentylene, 2,4-pentylene, 3,3-pentylene, 2-methyl-1,1-butylene, 2-methyl-1,2-butylene, 2-methyl-1,3-butylene, 2-methyl-1,4-butylene, 2-methyl-3,3-butylene, 2-methyl-3,4-butylene, 2-methyl-4,4-butylene, 2-ethyl-1,3-propylene, 2,2-dimethyl-1,1-propylene, 2,2-dimethyl-1,3-propylene, 1,1-hexylene, 1,2-hexylene, 1,3-hexylene, 1,4-hexylene, 1,5-hexylene, 1,6-hexylene, 2,2-hexylene, 2,3-hexylene, 2,4-hexylene, 2,5-hexylene, 3,3-hexylene, 3,4-hexylene, 2-methyl-1,1-pentylene, 2-methyl-1,2-pentylene, 2-methyl-1,3-pentylene, 2-methyl-1,4-pentylene, 2methyl-1,5-pentylene, 2-methyl-3,3-pentylene, 2-methyl-3,4-pentylene, 2-methyl-3,5-pentylene, 2-methyl-4,4-pentylene, 2-methyl-4,5-pentylene, 2-methyl-5,5-pentylene, 2-propyl-1,3- propylene, 3-methyl-1,1-pentylene, 3-methyl-1,2-pentylene, 3-methyl-1,3-pentylene, 3-methyl-1,4-pentylene, 3-methyl-1,5-pentylene, 3-methyl-2,2-pentylene, 3-methyl-2,3-pentylene, 3-methyl-2,4-pentylene, 2-ethyl-1,1-butylene, 2-ethyl-1,2-butylene, 2-ethyl-1,3-butylene, 2-ethyl-1,4-butylene, 2,3-dimethyl-1,1-butylene, 2,3-dimethyl-1,2-butylene, 2,3-dimethyl-1,3-butylene, 2,3-dimethyl-1,4-butylene, 2,3-dimethyl-2,3-butylene, 2-(2-propyl)-1,3-propylene, 2,2-dimethyl-1,1-butylene, 2,2-dimethyl-1,3-butylene, 2,2-dimethyl-1,4-butylene, 2,2-dimethyl-3,3-butylene, 2,2-dimethyl-3,4-butylene, 2,2-dimethyl-4,4-butylene and 2-methyl-2-ethyl-1,3-propylene, preferably methylene, 1,1-ethylene, 1,2-ethylene, 1,1-propylene and 1,1-propylene.

Those 1-amino-3-phenyluracils I are preferred in which the variables have the following meanings, to be precise in each case per se or in combination:

R¹ is hydrogen or fluorine, in particular fluorine;
Y is oxygen;
Z is —CH=N—O—($C_1$-$C_6$-alkyl), —CH=N—O—($C_1$-$C_6$-alkylene)—O—($C_1$-$C_6$-alkyl), —CH=C(Cl)—CO—O—($C_1$-$C_6$-alkyl), —CH=C(Br)—CO—O—($C_1$-$C_6$-alkyl) or —CH [X¹-($C_1$-$C_6$-alkyl)] [X²-($C_1$-$C_6$-alkyl)], X¹ and X² in particular being oxygen.
Preferred radicals R² to R¹¹ are hydrogen and methyl.

The compounds I are obtainable in various ways, eg. by one of the following processes:

A) Reaction of a 1H-3-phenyluracil of the formula II in the presence of a base with an electrophilic aminating reagent:

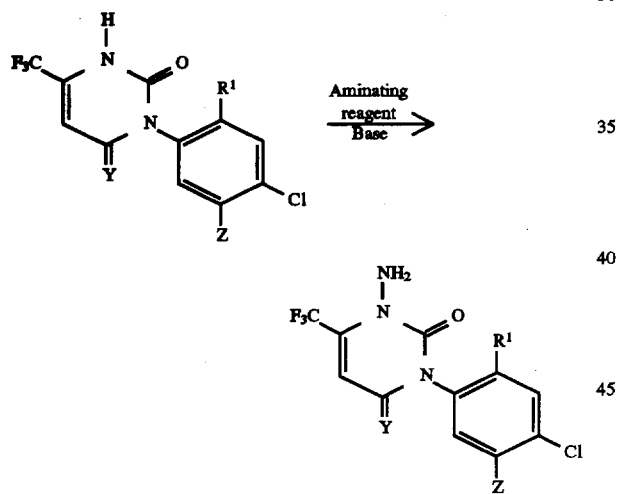

Until now, 2,4-dinitrophenoxyamine has proven particularly suitable as an aminating reagent, but eg. hydroxylamine-O-sulfonic acid (HOSA) can also be used, which is already known from the literature as an aminating reagent (cf. eg. E. Hofer et al., Synthesis (1983), 466; W. Friedrichsen et al., Heterocycles 20 (1983) 1271; H. Hart et al., Tetrahedron Lett. 25 (1984) 2073; B. Vercek et al., Monatsh. Chem. 114 (1983) 789; G. Sosnousky et al., Z. Naturforsch. 38 (1983) 884; R. S. Atkinson et al., J. Chem. Soc. Perkin Trans. 1987, 2787).

The amination can be carried out in a manner known per se (see eg. Sheradsky, Tetrahedron Lett. 1968, 1909; M. P. Wentland et al., J. Med. Chem. 27 (1984) 1103 and in particular EP-A 240 194, EP-A 476 697 and EP-A 517 181, where the amination of uracils is described).

Suitable bases are, for example, alkali metal carbonates such as potassium carbonate, alkali metal alkoxides such as sodium methoxide and potassium tert-butoxide or alkali metal hydrides such as sodium hydride.

The reaction is normally carried out in a polar solvent, eg. in dimethylformamide, N-methylpyrrolidOne, dimethyl sulfoxide or in ethyl acetate, which until now has proven particularly suitable.

Since the reaction is not detectably dependent on pressure, it is preferably carried out at normal pressure or under the autogenous pressure of the respective solvent.

The 1H-3-phenyluracils II are disclosed in WO 93/06090 or can be prepared by processes described there (in particular pages 56 and 57 and the preparation of the enamine ester and enamine carboxylate precursors on pages 74 to 81).

Transacetalization of an open-chain acetal of the formula V with a dihydric alcohol or thioalcohol of the formula III or IV in the presence of an acid as a catalyst in an inert solvent:

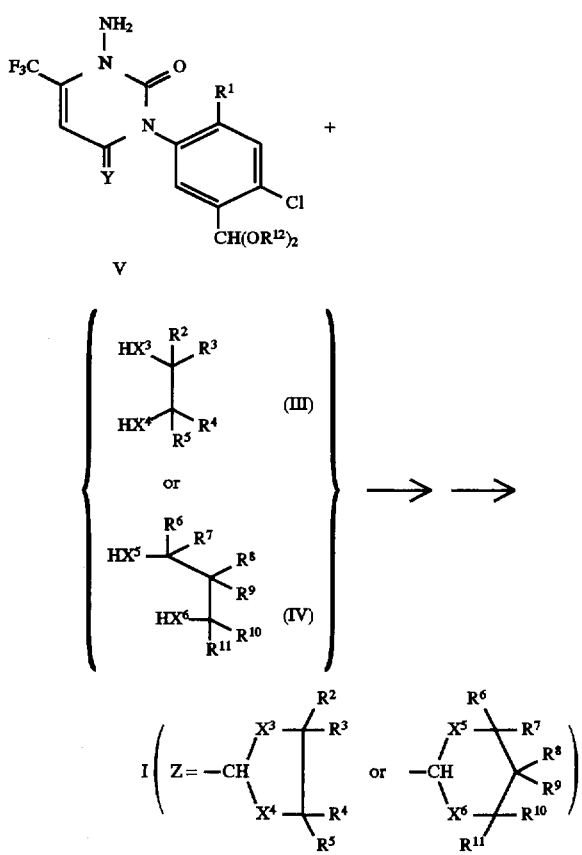

Reactions of this type are generally known, eg. from the following references:

H. Meerwein in Houben Weyl, Methoden Der Organischen Chemie [Methods of Organic Chemistry], Vol. VI/3, Stuttgart 1965, pages 250ff.;

J. H. Park et al., Chem. Lett. 1989, 629;

H. R. Pfaendler et al., Liebigs Ann. Chem. 1989, 691;

R. D. Walkup et al., Tetrahedron Lett. 1990, 6961.

The open-chain acetals V can be prepared eg. by method A) by aminating the corresponding 1H-derivatives VI:

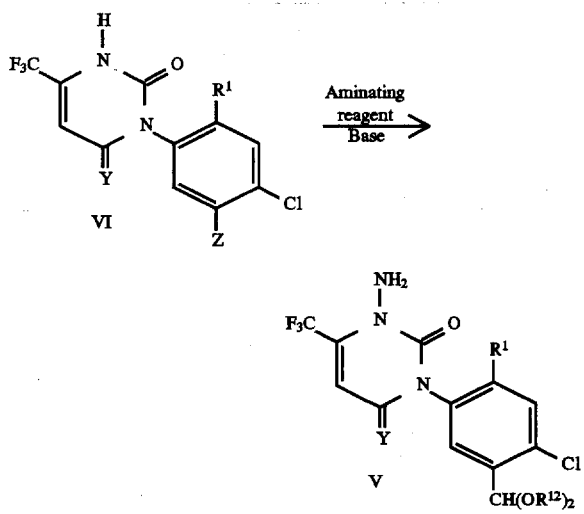

The 1H-derivatives VI are in turn obtainable by acetalization of 1H-3-(m-formylphenyl)uracils (cf. eg. WO 93/06090, pp. 61–63).

C) Sulfurization of 1-amino-3-phenyluracils of the formula I, where X is oxygen, with a suitable sulfurization reagent:

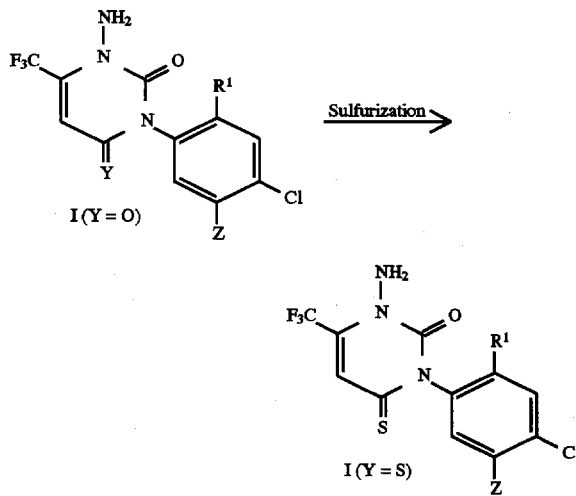

The reaction is as a rule carried out in an inert solvent or diluent, for example in an aromatic hydrocarbon such as toluene and o-, m- or p-xylene, in an ether such as diethyl ether, 1,2-dimethoxyethane and tetrahydrofuran, or in an organic amine such as pyridine.

Particularly highly suitable sulfurization reagents are phosphorus(V) sulfide and 2,4-bis(4-methoxyphenyl)-1,3,2,4-dithiadiphosphetane-2,4-dithione (Lawesson's reagent).

The amount of sulfurization reagent is not critical; customarily, 1 to 5 times the molar amount, based on the 3-phenylura-cil to be sulfurized, is sufficient for a substantially complete reaction.

Normally, the reaction temperature is from 20° to 200° C., preferably from 40° C. to the boiling point of the solvent.

If not stated otherwise, the starting materials and reagents needed for the preparation of the substituted 1-amino-3-phenyluracils I are known or can be prepared by methods known per se.

The working up of the respective reaction mixtures is as a rule carried out by methods known per se, for example by removing the solvent, partitioning the residue in a mixture of water and a suitable organic solvent and isolating the product from the organic phase.

Depending on the radical Z, the substituted 1-amino-3-phenyluracils can be obtained during preparation as isomer mixtures. These can be separated into the pure isomers, if desired, by the methods customary for this purpose, eg. by crystallization or chromatography on an optically active adsorbate. Pure optically active isomers can be synthesized, for example, from corresponding optically active starting materials.

The substituted 1-amino-3-phenyluracils I are suitable as herbicides, both as isomer mixtures and in the form of the pure isomers. They can control broad-leaved weeds and grass weeds very effectively in crops such as wheat, rice, maize, soybean and cotton without noticeably damaging the crop plants. This effect occurs especially at low application rates.

Depending on the particular application method, the substituted 1-amino-3-phenyluracils I or the herbicidal compositions containing them can additionally be employed in a further number of crop plants for eliminating undesired plants. Suitable crops, for example, are the following:

Allium cepa, Ananas comosus, Arachis hypogaea, Asparagus officinalis, Beta vulgaris spp. altissima, Beta vulgaris spp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago satira, Musa spp., Nicotiana tabacum (N. rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.

Moreover, the compounds I can also be employed in crops which have been made substantially resistant to the action of I or other herbicides by breeding and/or by means of genetic engineering methods.

In addition, the substituted 1-amino-3-phenyluracils I are also suitable for the desiccation and/or defoliation of plants. As desiccants, they are in particular suitable for the desiccation of the above-ground parts of crop plants such as potato, rape, sunflower and soybean. Completely mechanized harvesting of these important crop plants is thus made possible.

Of economic interest is also the facilitation of harvesting, which is made possible by the temporally concentrated dropping or reduction in the power of adhesion to the tree in the case of citrus fruits, olives or in the case of other species and varieties of pomaceous fruits, stone fruits and hard-shell dry fruit. The same mechanism, that is the promotion of the formation of separating tissue between fruit or leaf and stem part of the plant is also essential for a highly controllable defoliation of productive plants, in particular cotton.

Additionally, the shortening of the time interval in which the individual cotton plants become ripe leads to an enhanced fiber quality after harvesting.

The active compounds I and the herbicidal compositions containing them can be applied, for example, by spraying, atomizing, dusting, broadcasting or watering in the form of directly sprayable aqueous solutions, powders, suspensions, also high-percentage aqueous, oily or other suspensions or dispersions, emulsions, oil dispersions, pastes, dusting compositions, broadcasting compositions or granules. The application forms depend entirely on the intended uses; in each case if possible, they should guarantee the finest dispersion of the active compounds according to the invention.

Suitable inert auxiliaries for the production of directly sprayable solutions, emulsions, pastes or oil dispersions are essentially: mineral oil fractions of medium to high boiling point such as kerosene and diesel oil, also coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, n-propanol, butanol and cyclohexanol, ketones such as cyclohexanone, strongly polar solvents, eg. amines such as N-methylpyrrolidone and water.

Aqueous application forms can be prepared from emulsion concentrates, dispersions, pastes, wettable powders or water-dispersible granules by addition of water. For the production of emulsions, pastes or oil dispersions, the substrates as such or dissolved in an oil or solvent can be homogenized in water by means of wetting agents, adhesives, dispersants or emulsifiers. However, concentrates consisting of active substance, wetting agents, adhesives, dispersant or emulsifier and possibly solvents or oil can also be prepared, which are suitable for dilution with water.

Suitable surface-active substances are the alkali metal, alkaline earth metal or ammonium salts of aromatic sulfonic acids, eg. lignosulfonic acid, phenolsulfonic acid, naphthalenesulfonic acid and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols, as well as of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenol and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl esters, lauryl alcohol polyglycol ether acetate, sorbitol esters, lignin-sulfite waste liquors or methylcellulose.

Powder, broadcasting and dusting compositions can be produced by mixing or joint grinding of the active substances with a solid carrier.

Granules, eg. coated, impregnated and homogeneous granules can be produced by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground plastics, fertilizers, such as ammonium sulfate, ammonium phosphate, ammonium nitrate, ureas and vegetable products such as cereal meal, tree bark, wood and nutshell meal, cellulose powder or other solid carriers.

The concentrations of the active compounds I in the ready-to-apply preparations can be varied within wide ranges, for example from 0.01 to 95% by weight, preferably from 0.5 to 90% by weight. The active compounds are in this case normally employed in a purity of from 90% to 100%, preferably from 95% to 100% (according to NMR spectrum).

Examples of such preparations are:

I. a solution of 20 parts by weight of the compound No. 1.04 in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By fine dispersion of the mixture in 100,000 parts by weight of water, an aqueous dispersion is obtained which contains 0.02% by weight of the active compound;

II. a solution of 20 parts by weight of the compound No. 1.07 in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The fine dispersion of this mixture in 100,000 parts by weight of water yields an aqueous dispersion which contains 0.02% by weight of the active compound;

III. a solution of 20 parts by weight of the compound No. 1.25 in a mixture of 25 parts by weight of cyclohexanone, 65 parts by weight of a mineral oil fraction of boiling point 210° to 280° C. and 10 parts by weight of the addition product of 40 mol of ethylene oxide to 1 mol of castor oil. The fine dispersion of this mixture in 100,000 parts by weight of water yields an aqueous dispersion which contains 0.02% by weight of the active compound;

IV. a mixture ground in a hammer mill of 20 parts by weight of the compound No. 1.95, 3 parts by weight of the sodium salt of diisobutylnaphthalene-$\alpha$-sulfonic acid, 17 parts by weight of the sodium salt of the lignosulfonic acid from a sulfite waste liquor and 60 parts by weight of powdered silica gel. By fine dispersion of the mixture in 20,000 parts by weight of water, a spray liquor is obtained which contains 0.1% by weight of the active compound;

V. a mixture of 3 parts by weight of the compound No. 1.98 and 97 parts by weight of finely divided kaolin. This dusting composition contains 3% by weight of active compound;

VI. a stable oily dispersion of 20 parts by weight of the compound No. 2.05, 2 parts by weight of the calcium salt of dodecylbenzenesulfonic acid, 8 parts by weight of fatty alcohol polyglycol ether, 2 parts by weight of the sodium salt of a phenol-urea-formaldehyde condensate and 68 parts by weight of a paraffinic mineral oil.

The application of the active compounds I or of the herbicidal agents can be carried out pre-emergence or post-emergence. If the active compounds are less tolerable to certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The application rates of active compound are, depending on the target to be controlled, time of year and stage of growth from 0.0001 to 2.0, preferably from 0.001 to 1 kg/ha of active substance (a.s.).

For widening the spectrum of action and for achieving synergistic effects, the substituted 1-amino-3-phenyluracils I can be mixed with numerous representatives of other herbicidal or growth-regulating active compound groups and applied together. For example, suitable mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry eg. a carboxyl or carbimino group in the 2-position, quinolinecarboxylic acid derivatives, imidazolinones, sulfonamides, sulfonylureas, aryloxy- and heteroaryloxyphenoxypropionic acids as well as their salts, esters and amides, inter alia.

It may additionally be of use to mix the substituted 1-amino-3-phenyluracils I; on their own or in combination with other herbicides, additionally with further plant protection compositions and to apply them together, for example with pesticides, compositions against phytopathogenic fungi and against bacteria. These compositions can be admixed to the compositions according to the invention in a weight ratio from 1:100 to 100:1, if desired additionally only immediately before application (tank-mix). Additionally of interest is the miscibility with mineral salt solutions, which are employed for the elimination of nutritional and trace element deficiencies. Non-phytotoxic oils and oil concentrates can also be added.

PREPARATION EXAMPLES

Example 1

1-Amino-3-(4-chloro-3-methoxyiminomethylphenyl)
-2,4-dioxo-6-trifluoromethyl-1,2,3,4-
tetrahydropyrimidine (Tab. 1, No. 1.04)

0.38 g (16 mmol) of sodium hydride in 50 ml of anhydrous dimethylformamide was treated dropwise at 0°–5° C. with a solution of 5.0 g (14 mmol) of 3-(4-chloro-3-methoxyiminomethylphenyl)-2,4-dioxo-6-trifluoromethyl-1,2,3,4-tetrahydropyrimidine in 50 ml of anhydrous dimethylformamide. A solution of 2.8 g (14 mmol) of 2,4-dinitrophenoxyamine in 50 ml of anhydrous dimethylformamide was added dropwise to this mixture after 10 minutes, after which it was stirred for 60 hours at 20°–25° C. and for 6 hours at 50° C. For working up, the cooled reaction mixture was poured into 800 ml of ice water. The aqueous phase was extracted three times with 200 ml of ethyl acetate each time. The ethyl acetate extracts were then dried over sodium sulfate and concentrated. After chromatographic purification of the crude product on silica gel (eluent: cyclohexane/ethyl acetate/triethylamine 79:20:1), 1.5 g (29%) of a colorless oil were obtained.

$^1$H-NMR (250 MHz, in CDCl$_3$): δ[ppm]=3.97(s,3H), 4.58 (s,2H), 6.28(s,1H), 7.14(dd,1H), 7.50(d,1H), 7.80(d,1H), 8.45(s,1H).

Example 2

1-Amino-3-(4-chloro-3-ethoxyiminomethylphenyl)-
2,4-dioxo-6-trifluoromethyl-1,2,3,4-
tetrahydropyrimidine (Tab. 1, No. 1.07)

0.38 g (16 mmol) of sodium hydride in 25 mi of anhydrous dimethylformamide was treated dropwise at 0°–5° C. with a solution of 5.0 g (14 mmol) of 3-(4-chloro-3-ethoxyiminomethylphenyl)-2,4-dioxo-6-trifluoromethyl-1, 2,3,4-tetrahydropyrimidine in 25 ml of anhydrous dimethylformamide. A solution of 2.8 g (14 mmol) of 2,4-dinitrophenoxyamine in 50 ml of anhydrous dimethylformamide was added dropwise to this mixture after 10 minutes, after which it was stirred for 20 hours at 20°–25° C.

For working up, the reaction mixture was poured into 500 ml of water. The aqueous phase was then extracted three times with 150 ml of ethyl acetate each time. The ethyl acetate extracts were dried over sodium sulfate and concentrated. After chromatographic purification of the crude product on silica gel (eluent: cyclohexane/ethyl acetate 4:1), 2.4 g (46%) of a colorless oil were obtained.

$^1$H-NMR (250 MHz, in CDCl$_3$): δ [ppm]=1.32(t,3H), 4.20(q,3H), 4.60(s,2H), 6.27(s,1H), 7.12(dd, 1H), 7.50(d, 1H), 7.80(d, 1H), 8.46(s,1H).

Example 3

1-Amino-3-(4-chloro-5-ethoxyiminomethyl-2-
fluorophenyl)-2,4-dioxo-6-trifluoromethyl-1,2,3,4-
tetrahydropyrimidine (Tab. 1, No. 1.08)

In a similar manner to Example 2, starting from 5.3 g (14 mmol) of 3-(4-chloro-5-ethoxyiminomethyl-2-fluorophenyl)-2,4-dioxo-6-trifluoromethyl-1,2,3,4-tetrahydropyrimidine, 1.4 g (25%) of the desired product were obtained as a colorless oil.

$^1$H-NMR (250 MHz, in CDCl$_3$): δ [ppm]=1.32(t,3H), 4.22(q,2H), 4.60(s,br.,2H), 6.28(s,1H), 7.32(d,1H), 7.87(d, 1H), 8.42(s,1H).

Example 4

1-Amino-3-(4-chloro-3-
ethoxycarbonylmethyleneoxyiminomethyl-phenyl)-
2,4-dioxo-6-trifluoromethyl-1,2,3,4-
tetrahydropyrimidine (Tab. 1, No. 1.25)

Preparation was carried out in a similar manner to Example 2, starting from 11.2 g (27.0 mmol) of 3-(4-chloro-3-ethoxycarbonyl-methyleneoxyiminomethylphenyl)-2,4-dioxo-6-trifluoromethyl-1,2,3,4-tetrahydropyrimidine. Yield: 5.1 g (44%) of colorless crystals of melting point 163°–164° C.

Example 5

1-Amino-3-(4-chloro-3-dimethoxymethylphenyl)-2,
4-dioxo-6-trifluoromethyl-1,2,3,4-
tetrahydropyrimidine (Tab. 1, No. 1.95)

In a similar manner to Example 2, starting from 4.4 g (12 mmol) of 3-(4-chloro-3-dimethoxymethylphenyl)-2,4-dioxo-6-trifluoromethyl-1,2,3,4-tetrahydropyrimidine 3.1 g (68%) of the desired product were obtained as a colorless oil.

$^1$H-NMR (250 MHz, in CDCl$_3$): δ [ppm]=3.35(s,6H), 4.58(s,2H), 5.64(s,1H), 6.25(s,1H), 7.14(dd,1H), 7.48–7.54 (m,2H).

Example 6

1-Amino-3-(4-chloro-5-dimethoxymethyl-2-
fluorophenyl)-2,4-dioxo-6-trifluoromethyl-1,2,3,4-
tetrahydropyrimidine (Tab. 1, No. 1.96)

Preparation was carried out in a similar manner to Example 2, starting from 6.7 g (17.5 mmol) of 3-(4-chloro-5-dimethoxymethyl-2-fluoraphenyl)-2,4-dioxo-6-trifluoromethyl-1,2,3,4-tetrahydropyrimidine. Yield: 1.8 g (26%) of colorless crystals of melting point 118°–119° C.

Example 7

1-Amino-3-(4-chloro-3-diethoxymethylphenyl)-2,4-
dioxo-6-trifluoromethyl-1,2,3,4-
tetrahydropyrimidine (Tab. 1, No. 1.98)

In a similar manner to Example 2, starting from 6.1 g (15.5 mmol) of 3-(4-chloro-3-diethoxymethylphenyl)-2,4- dioxo-6-trifluoromethyl-1,2,3,4-tetrahydropyrimidine 5.5 g (87%) of colorless crystals of melting point 80°–81° C. and about 85% purity were obtained.

¹H-NMR (250 MHz, in CDCl₃): δ [ppm]=1.21(t,6H), 3.55–3.67(m,4H), 4.59(s,2H), 5.74(s,1H), 6.27(s,1H), 7.12 (dd,1H), 7.50.(d,1H), 7.55(d,1H).

Example 8

1-Amino-3-[4-chloro-3-(4-methyl-1,3-dithiolan-2-yl)phenyl]-2,4-dioxo-6-trifluoromethyl-1,2,3,4-tetrahydropyrimidine (Tab. 1, No. 1.137)

2.5 g (6.1 mmol) of 1-amino-3-(4-chloro-3-diethoxymethyl-phenyl)-2,4-dioxo-6-trifluoromethyl-1,2,3,4-tetrahydropyrimidine, 2.0 g (18 mmol) of 1,2-propanedithiol and 50 mg of p-toluenesulfonic acid were refluxed in 100 ml of anhydrous toluene for six hours. After cooling, the mixture was washed with 10% strength sodium hydrogen carbonate solution and water, dried over sodium sulfate, concentrated and dried for 48 hours at reduced pressure. 2.1 g (80%) of a colorless oil were thus obtained, which is a 1:1 mixture of the two diastereomers.

¹H-NMR (250 MHz, in CDCl₃): δ [ppm]=1.47 (d,3H), 1.52 (d,3H), 2.98–3.05 (m,2H), 3.28–3.48 (m,2H), 3.92–4.00 (m,2H), 4.25–4.75 (br.,4H), 6.04 (s,1H), 6.05 (s,1H), 6.28 (s,2H), 7.04–7.09 (m,2H), 7.46–7.52 (m,2H), 7.76 (d, 1H), 7.86 (d, 1H).

Example 9

1-Amino-3-(4-chloro-2-fluoro-3-methoxyiminomethylphenyl)-2,4-dioxo-6-trifluoromethyl-1,2,3,4-tetrahydropyrimidine (Tab. 1, No. 1.05)

Potassium carbonate (132 g) and 2,4-dinitrophenoxyamine (104 g) were added to a solution of 3-(4-chloro-2-fluoro-3-methoxyiminomethylphenyl)-2,4-dioxo-6-trifluoromethyl-1,2,3,4-tetrahydropyrimidine (175 g) in 1 l of ethyl acetate, after which the reaction mixture was stirred for 10 hours at 50° C. and then cooled. The resulting solid portion was separated off and washed with diisopropyl ether. After combining the clear reaction solution and the ether phase, the mixture was washed once with water, dried over sodium sulfate and concentrated. The crude product was recrystallized from 200 ml of diisopropyl ether. Yield: 150 g.

Example 10

1-Amino-3-(4-chloro-2-fluoro-5-methoxyiminomethylphenyl)-2-oxo-4-thiono-6-trifluoromethyl-1,2,3,4-tetrahydropyrimidine
(Compound 2.05)

3.4 g of Lawesson's reagent were added to a solution of 1-amino-3-(4-chloro-2-fluoro-5-methoxyiminomethylphenyl)-2,4-dioxo-6-trifluoromethyl-1,2,3,4-tetrahydropyrimidine (3.8 g) in 100 ml of toluene. After refluxing for 12 hours, the solvent was removed and the crude product obtained was purified by chromatography. Yield: 2.2 g; m.p.: 172°–174° C.

The following Tables 1 and 2 show further compounds I which were prepared or can be prepared in the same manner:

TABLE 1

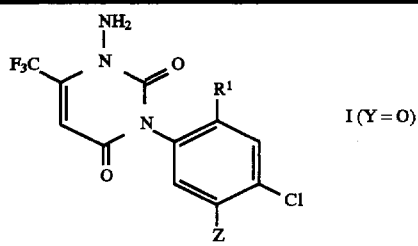

I (Y=O)

| Ex. No. | R¹ | Z | M.p. or ¹H-NMR (CDCl₃; δ [ppm]) |
|---|---|---|---|
| 1.01 | H | —CH=N—OH | |
| 1.02 | F | —CH=N—OH | |
| 1.03 | Cl | —CH=N—OH | |
| 1.04 | H | —CH=N—OCH₃ | 3.97(s, 3H), 4.58(s, 2H), 6.28(s, 1H), 7.14(dd, 1H), 7.50(d, 1H), 7.80(d, 1H), 8.45(s, 1H) |
| 1.05 | F | —CH=N—OCH₃ | 3.97(s, 3H), 4.60(s, br., 2H), 7.87(d, 1H), 8.39(s, 1H) |
| 1.06 | Cl | —CH=N—OCH₃ | |
| 1.07 | H | —CH=N—OC₂H₅ | 1.32(t, 3H), 4.20(q, 3H), 4.60(s, 2H), 6.27(s, 1H), 7.12(dd, 1H), 7.50(d, 1H), 7.80(d, 1H), 8.46(s, 1H) |
| 1.08 | F | —CH=N—OC₂H₅ | 1.32(t, 3H), 4.22(q, 2H), 4.60(s, br., 2H), 6.28(s, 1H), 7.32(d, 1H), 7.87(d, 1H), 8.42(s, 1H) |
| 1.09 | Cl | —CH=N—OC₂H₅ | |

TABLE 1-continued

I (Y = O)

| Ex. No. | R¹ | Z | M.p. or ¹H-NMR (CDCl₃; δ [ppm]) |
|---|---|---|---|
| 1.10 | H | —CH=N—OCH₂—C₂H₅ | |
| 1.11 | F | —CH=N—OCH₂—C₂H₅ | |
| 1.12 | Cl | —CH=N—OCH₂—C₂H₅ | |
| 1.13 | H | —CH=N—OCH(CH₃)₂ | |
| 1.14 | F | —CH=N—OCH(CH₃)₂ | |
| 1.15 | Cl | —CH=N—OCH(CH₃)₂ | |
| 1.16 | H | —CH=N—OCH₂—CH₂—OCH₃ | |
| 1.17 | F | —CH=N—OCH₂—CH₂—OCH₃ | 121–123° C. |
| 1.18 | Cl | —CH=N—OCH₂—CH₂—OCH₃ | |
| 1.19 | H | —CH=N—OCH₂—CH₂—OC₂H₅ | |
| 1.20 | F | —CH=N—OCH₂—CH₂—OC₂H₅ | |
| 1.21 | Cl | —CH=N—OCH₂—CH₂—OC₂H₅ | |
| 1.22 | H | —CH=N—OCH₂—CO—OCH₃ | 142° C. |
| 1.23 | F | —CH=N—OCH₂—CO—OCH₃ | |
| 1.24 | Cl | —CH=N—OCH₂—CO—OCH₃ | |
| 1.25 | H | —CH=N—OCH₂—CO—OC₂H₅ | 163–164° C. |
| 1.26 | F | —CH=N—OCH₂—CO—OC₂H₅ | |
| 1.27 | Cl | —CH=N—OCH₂—CO—OC₂H₅ | |
| 1.28 | H | —CH=N—OCH(CH₃)—CO—OCH₃ | |
| 1.29 | F | —CH=N—OCH(CH₃)—CO—OCH₃ | |
| 1.30 | Cl | —CH=N—OCH(CH₃)—CO—OCH₃ | |
| 1.31 | H | —CH=N—OCH(CH₃)—CO—OC₂H₅ | |
| 1.32 | F | —CH=N—OCH(CH₃)—CO—OC₂H₅ | |
| 1.33 | Cl | —CH=N—OCH(CH₃)—CO—OC₂H₅ | |
| 1.34 | H | —CH=N—OCH₂—CO—OCH₂—CH₂—OCH₃ | |
| 1.35 | F | —CH=N—OCH₂—CO—OCH₂—CH₂—OCH₃ | |
| 1.36 | Cl | —CH=N—OCH₂—CO—OCH₂—CH₂—OCH₃ | |
| 1.37 | H | —CH=N—OCH₂—CO—OCH₂—CH₂—OC₂H₅ | |
| 1.38 | F | —CH=N—OCH₂—CO—OCH₂—CH₂—OC₂H₅ | |
| 1.39 | Cl | —CH=N—OCH₂—CO—OCH₂—CH₂—OC₂H₅ | |
| 1.40 | H | —CH=N—OCH(CH₃)—CO—OCH₂—CH₂—OCH₃ | |
| 1.41 | F | —CH=N—OCH(CH₃)—CO—OCH₂—CH₂—OCH₃ | |
| 1.42 | Cl | —CH=N—OCH(CH₃)—CO—OCH₂—CH₂—OCH₃ | |
| 1.43 | H | —CH=N—OCH(CH₃)—CO—OCH₂—CH₂—OC₂H₅ | |
| 1.44 | F | —CH=N—OCH(CH₃)—CO—OCH₂—CH₂—OC₂H₅ | |
| 1.45 | Cl | —CH=N—OCH(CH₃)—CO—OCH₂—CH₂—OC₂H₅ | |
| 1.46 | H | —CH=CH—COOCH₃ | |
| 1.47 | F | —CH=CH—COOCH₃ | |
| 1.48 | Cl | —CH=CH—COOCH₃ | |
| 1.49 | H | —CH=CH—COOC₂H₅ | |
| 1.50 | F | —CH=CH—COOC₂H₅ | |
| 1.51 | Cl | —CH=CH—COOC₂H₅ | |
| 1.52 | H | —CH=CH—CO—OCH₂CH₂—OCH₃ | |
| 1.53 | F | —CH=CH—CO—OCH₂CH₂—OCH₃ | |
| 1.54 | Cl | —CH=CH—CO—OCH₂CH₂—OCH₃ | |
| 1.55 | H | —CH=CH—CO—OCH₂CH₂—OC₂H₅ | |
| 1.56 | F | —CH=CH—CO—OCH₂CH₂—OC₂H₅ | |
| 1.57 | Cl | —CH=CH—CO—OCH₂CH₂—OC₂H₅ | |
| 1.58 | H | —CH=C(Cl)—CO—OCH₃ | |
| 1.59 | F | —CH=C(Cl)—CO—OCH₃ | |
| 1.60 | Cl | —CH=C(Cl)—CO—OCH₃ | |
| 1.61 | H | —CH=C(Cl)—CO—OC₂H₅ | 183–185° C. |
| 1.62 | F | —CH=C(Cl)—CO—OC₂H₅ | |
| 1.63 | Cl | —CH=C(Cl)—CO—OC₂H₅ | |
| 1.64 | H | —CH=C(Cl)—CO—OCH₂CH₂—OCH₃ | |
| 1.65 | F | —CH=C(Cl)—CO—OCH₂CH₂—OCH₃ | |
| 1.66 | Cl | —CH=C(Cl)—CO—OCH₂CH₂—OCH₃ | |
| 1.67 | H | —CH=C(Cl)—CO—OCH₂CH₂—OC₂H₅ | |
| 1.68 | F | —CH=C(Cl)—CO—OCH₂CH₂—OC₂H₅ | |
| 1.69 | Cl | —CH=C(Cl)—CO—OCH₂CH₂—OC₂H₅ | |
| 1.70 | H | —CH=C(CH₃)—CO—OCH₃ | |
| 1.71 | F | —CH=C(CH₃)—CO—OCH₃ | |
| 1.72 | Cl | —CH=C(CH₃)—CO—OCH₃ | |

TABLE 1-continued

I (Y = O)

| Ex. No. | R¹ | Z | M.p. or ¹H-NMR (CDCl₃; δ [ppm]) |
|---|---|---|---|
| 1.73 | H | —CH=C(CH₃)—CO—OC₂H₅ | |
| 1.74 | F | —CH=C(CH₃)—CO—OC₂H₅ | |
| 1.75 | Cl | —CH=C(CH₃)—CO—OC₂H₅ | |
| 1.76 | H | —CH=C(CH₃)—CO—OCH₂CH₂—OCH₃ | |
| 1.77 | F | —CH=C(CH₃)—CO—OCH₂CH₂—OCH₃ | |
| 1.78 | Cl | —CH=C(CH₃)—CO—OCH₂CH₂—OCH₃ | |
| 1.79 | H | —CH=C(CH₃)—CO—OCH₂CH₂—OC₂H₅ | |
| 1.80 | F | —CH=C(CH₃)—CO—OCH₂CH₂—OC₂H₅ | |
| 1.81 | Cl | —CH=C(CH₃)—CO—OCH₂CH₂—OC₂H₅ | |
| 1.82 | H | —CH=C(Br)—CO—OCH₃ | |
| 1.83 | F | —CH=C(Br)—CO—OCH₃ | 183–184° C. |
| 1.84 | Cl | —CH=C(Br)—CO—OCH₃ | |
| 1.85 | H | —CH=C(Br)—CO—OC₂H₅ | |
| 1.86 | F | —CH=C(Br)—CO—OC₂H₅ | |
| 1.87 | Cl | —CH=C(Br)—CO—OC₂H₅ | |
| 1.88 | H | —CH=C(Br)—CO—OCH₂CH₂—OCH₃ | |
| 1.89 | F | —CH=C(Br)—CO—OCH₂CH₂—OCH₃ | |
| 1.90 | Cl | —CH=C(Br)—CO—OCH₂CH₂—OCH₃ | |
| 1.91 | H | —CH=C(Br)—CO—OCH₂CH₂—OC₂H₅ | |
| 1.93 | F | —CH=C(Br)—CO—OCH₂CH₂—OC₂H₅ | |
| 1.94 | Cl | —CH=C(Br)—CO—OCH₂CH₂—OC₂H₅ | |
| 1.95 | H | —CH(OCH₃)₂ | 3.35(s, 6H), 4.58(s, 2H), 5.64(s, 1H), 6.25(s, 1H), 7.14(dd, 1H), 7.48–7.54(m, 2H) |
| 1.96 | F | —CH(OCH₃)₂ | 118–119° C. |
| 1.97 | Cl | —CH(OCH₃)₂ | |
| 1.98 | H | —CH(OC₂H₅)₂ | 80–81° C. 1.21(t, 6H), 3.55–3.67(m, 4H), 4.59(s, 2H), 5.74(s, 1H), 6.27(s, 1H), 7.12(dd, 1H), 7.50(d, 1H), 7.55(d, 1H) |
| 1.99 | F | —CH(OC₂H₅)₂ | |
| 1.100 | Cl | —CH(OC₂H₅)₂ | |
| 1.101 | H | —CH(OCH₂—C₂H₅)₂ | |
| 1.102 | F | —CH(OCH₂—C₂H₅)₂ | |
| 1.103 | Cl | —CH(OCH₂—C₂H₅)₂ | |
| 1.104 | H | —CH(SCH₃)₂ | |
| 1.105 | F | —CH(SCH₃)₂ | |
| 1.106 | Cl | —CH(SCH₃)₂ | |
| 1.107 | H | —CH(SC₂H₅)₂ | |
| 1.108 | F | —CH(SC₂H₅)₂ | |
| 1.109 | Cl | —CH(SC₂H₅)₂ | |
| 1.110 | H | —CH(SCH₂—C₂H₅)₂ | |
| 1.111 | F | —CH(SCH₂—C₂H₅)₂ | |
| 1.112 | Cl | —CH(SCH₂—C₂H₅)₂ | |
| 1.113 | H | -(1,3-Dioxolan-2-yl) | |
| 1.114 | F | -(1,3-Dioxolan-2-yl) | 163–165° C. |
| 1.115 | Cl | -(1,3-Dioxolan-2-yl) | |
| 1.116 | H | -(4-Methyl-1,3-dioxolan-2-yl) | |
| 1.117 | F | -(4-Methyl-1,3-dioxolan-2-yl) | |
| 1.118 | Cl | -(4-Methyl-1,3-dioxolan-2-yl) | |
| 1.119 | H | -(4-Vinyl-1,3-dioxolan-2-yl) | |
| 1.120 | F | -(4-Vinyl-1,3-dioxolan-2-yl) | |
| 1.121 | Cl | -(4-Vinyl-1,3-dioxolan-2-yl) | |
| 1.122 | H | -(4-Methoxycarbonyl-1,3-dioxolan-2-yl) | |
| 1.123 | F | -(4-Methoxycarbonyl-1,3-dioxolan-2-yl) | |
| 1.124 | Cl | -(4-Methoxycarbonyl-1,3-dioxolan-2-yl) | |
| 1.125 | H | -(4-Ethoxycarbonyl-1,3-dioxolan-2-yl | |
| 1.126 | F | -(4-Ethoxycarbonyl-1,3-dioxolan-2-yl | |
| 1.127 | Cl | -(4-Ethoxycarbonyl-1,3-dioxolan-2-yl | |
| 1.128 | H | -(3-Oxa-1-thiolan-2-yl) | |
| 1.129 | F | -(3-Oxa-1-thiolan-2-yl) | |
| 1.130 | Cl | -(3-Oxa-1-thiolan-2-yl) | |
| 1.131 | H | -(4-Methyl-3-oxa-1-thiolan-2-yl) | |
| 1.132 | F | -(4-Methyl-3-oxa-1-thiolan-2-yl) | |

TABLE 1-continued $$\text{Structure: } F_3C\text{-substituted uracil with } NH_2, \text{ attached to phenyl ring with } R^1 \text{ and } Cl, Z \text{ substituents} \quad I(Y=O)$$

| Ex. No. | R¹ | Z | M.p. or ¹H-NMR (CDCl₃; δ [ppm]) |
|---|---|---|---|
| 1.133 | Cl | -(4-Methyl-3-oxa-1-thiolan-2-yl) | |
| 1.134 | H | -(1,3-Dithiolan-2-yl) | |
| 1.135 | F | -(1,3-Dithiolan-2-yl) | |
| 1.136 | Cl | -(1,3-Dithiolan-2-yl) | |
| 1.137 | H | -(4-Methyl-1,3-dithiolan-2-yl) | 1.47(d, 3H), 1.52(d, 3H), 2.98–3.05(m, 2H), 3.28–3.48(m, 2H), 3.92–4.00(m, 2H), 4.25–4.75(br., 4H), 6.04(s, 1H), 6.05(s, 1H), 6,28(s, 2H), 7.04–7.09(m, 2H), 7.46–7.52 (m, 2H), 7.76(d, 1H), 7.86(d, 1H) Diastereomer mixture (about 1:1) |
| 1.138 | F | -(4-Methyl-1,3-dithiolan-2-yl) | |
| 1.139 | Cl | -(4-Methyl-1,3-dithiolan-2-yl) | |
| 1.140 | H | -(1,3-Dioxan-2-yl) | |
| 1.141 | F | -(1,3-Dioxan-2-yl) | 167–168° C. |
| 1.142 | Cl | -(1,3-Dioxan-2-yl) | |
| 1.143 | H | -(3-Oxa-1-thian-2-yl) | |
| 1.144 | F | -(3-Oxa-1-thian-2-yl) | |
| 1.145 | Cl | -(3-Oxa-1-thian-2-yl) | |
| 1.146 | H | -(1,3-Dithian-2-yl) | |
| 1.147 | F | -(1,3-Dithian-2-yl) | |
| 1.148 | Cl | -(1,3-Dithian-2-yl) | |
| 1.149 | H | -(4-Methyl-1,3-dithian-2-yl) | |
| 1.150 | F | -(4-Methyl-1,3-dithian-2-yl) | |
| 1.151 | Cl | -(4-Methyl-1,3-dithian-2-yl) | |

Examples of 1-amino-3-phenyluracils I where Y=sulfur are the compounds 2.01 to 2.151, in which the radicals R¹ and Z have the same meaning as for the corresponding compounds 1.01 to 1.151 (where Y=oxygen) of Table 1.

Physical data for the compounds I where Y=sulfur:
Compound 2.04: >130° C. (dec.)
Compound 2.05: see Preparation Example 10

Use examples (herbicidal activity)

It was possible to show the herbicidal action of the substituted 1-amino-3-phenyluracils I by greenhouse tests:

The cultivation containers used were plastic flower pots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly sprayed to promote germination and growth, and then covered with transparent plastic hoods until the plants had taken root. This covering causes uniform germination of the test plants if this has not been adversely affected by the active compounds. The application rate for pre-emergence application was 62.5 and 31.3 g/ha of active substance.

For post-emergence treatment, the test plants were raised, depending on growth form, up to a growth height of from 3 to 15 cm, and only then treated with the active compounds suspended or emulsified in water. For this purpose, the test plants were either sown directly and cultivated in the same containers or they were first raised separately as seedlings and transplanted into the test containers a few days before treatment. The application rate for post-emergence treatment was 31.3 and 15.6 g of active substance per ha.

The plants were kept in a species-specific manner at 10°–25° C. or 20°–35° C. The test period extended over 2 to 4 weeks. During this time, the plants were tended and their reaction to the individual treatments was evaluated.

Assessment was carried out on a scale from 0 to 100. 100 in this case means no emergence of the plants or complete destruction at least of the above-ground parts and 0 means no damage or normal course of growth.

The plants used in the greenhouse tests consist of the following species:

| Latin name | Common name |
|---|---|
| Abutilon theophrasti | velvet leaf |
| Amaranthus retroflexus | redroot pigweed |
| Ipomoea spp. | morning glory |
| Polygonum persicaria | lady's thumb |
| Solanum nigrum | black nightshade |

Post-emergence, broad-leaved plants were very well controlled using the compounds of Examples 1.96 and 1.08 at 0.0313 and 0.0156 kg/ha of a.s.

Pre-emergence, grass weeds or broad-leaved plants were very well controlled using the compounds of Examples 1.96 and 1.08 at 0.0625 and 0.0313 or 0.0313 and 0.0156 kg/ha of a.s. respectively.

The superior herbicidal action of the 1-amino-3-phenyluracils I according to the invention compared with structurally similar uracils known from WO 93/06090 follows from the data in Tables 3 to 5.

The test substances used were

| Structure | Label |
|---|---|
| (structure with NH₂, F₃C, N, O, F, Cl, CH=N—OCH₃) | No. 1.05 (according to the invention) |
| (structure with CH₃, F₃C, N, O, F, Cl, CH=N—OCH₃) | Comparison compound A (No. 1.68 from WO 93/06090) |
| (structure with NH₂, F₃C, N, O, F, Cl, CH=N—OC₂H₅) | No. 1.08 (according to the invention) |
| (structure with CH₃, F₃C, N, O, F, Cl, CH=N—OC₂H₅) | Comparison compound B (No. 1.70 from WO 93/06090) |
| (structure with NH₂, F₃C, N, O, F, Cl, CH(OCH₃)₂) | No. 1.96 (according to the invention) |
| (structure with CH₃, F₃C, N, O, F, Cl, CH(OCH₃)₂) | Comparison compound C (cf. WO 93/06090: Structure I-2 where W = 4. Radical on p. 45) |

TABLE 3

Herbicidal action of the compounds No. 1.05 and A on pre-emergence application of 0.0039 kg/ha of active substance; greenhouse test

| | Test plants and damage [%] | | |
|---|---|---|---|
| No. | Setaria faberii | Setaria italica | Setaria viridis |
| 1.05 | 98 | 75 | 90 |
| A | 20 | 60 | 75 |

TABLE 4

Herbicidal action of the compounds No. 1.08 and B on pre-emergence application of 0.0078 kg/ha of active substance; greenhouse test.

| | Test plants and damage [%] | | |
|---|---|---|---|
| No. | Echinochloa crus-galli | Setaria faberii | Setaria italica |
| 1.08 | 50 | 90 | 90 |
| B | 30 | 35 | 20 |

TABLE 5

Herbicidal action of the compounds No. 1.96 and C on pre-emergence application of 0.0078 kg/ha of active substance; greenhouse test

| | Test plants and damage [%] | |
|---|---|---|
| No. | Echinochloa crus-galli | Setaria faberii |
| 1.96 | 90 | 100 |
| C | 40 | 10 |

Use examples (desiccant/defoliant activity)

The test plants used were young, 4-leaved (without seed leaves) cotton plants of the variety Stoneville 825, which were raised under greenhouse conditions (rel. atmospheric humidity 50 to 70%; day/night temperature 27/20° C.).

The young cotton plants were subjected to foliar treatment until dripping wet with aqueous preparations of the active compounds indicated (with addition of 0.15% by weight of the fatty alcohol alkoxylate Plurafac LF 700, based on the spray liquor). The amount of water applied was the equivalent of 1000 l/ha. After 13 days, the number of leaves shed and the degree of defoliation was determined in %. In the case of the untreated control plants, no leaf fall occurred.

We claim:

1. A substituted 1-amino-3-phenyluracil of the formula I

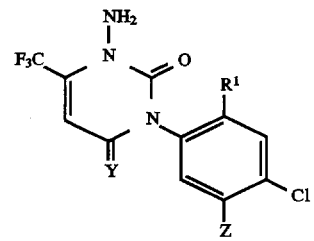

where the variables have the following meanings:
R¹ is hydrogen, fluorine or chlorine;
Y is oxygen or sulfur;
Z is —CH=N—OH, —CH=N—O—($C_1$-$C_6$-alkyl), —CH=N—O—(C$_1$-C$_6$-alkylene)—O —(C$_1$-C$_6$-alkyl),
—CH=N—O—CH$_2$—COOH, —CH=N—O—CH(C$_1$-C$_6$-alkyl)—COOH,
—CH=N—O—CH$_2$—CO—O—(C$_1$-C$_6$-alkyl),
—CH=N—O—CH (C$_1$-C$_6$-alkyl)—CO—O—(C$_1$-C$_6$-alkyl),
—CH=N—O—CH$_2$—CO—O—(C$_1$-C$_6$-alkylene)—O—(C$_1$-C$_6$-alky),
—CH=N—O—CH (C$_1$-C$_6$-alkyl)—CO—O—(C$_1$-C$_6$-alkylene)—O—(C$_1$-C$_6$-alkyl),
—CH[X$^1$-(C$_1$-C$_6$-alkyl)] [X$^2$-(C$_1$-C$_6$-alkyl)] or a radical

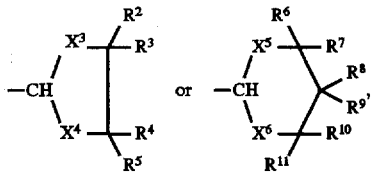

where
X$^1$–X$^6$ in each case are oxygen or sulfur and
R$^2$–R$^{11}$ in each case are hydrogen, C$_1$–C$_4$-alkyl, vinyl or C$_1$–C$_4$alkoxycarbonyl.

2. A herbicidal composition, containing at least one liquid and/or solid carrier and, if desired, at least one adjuvant as well as a herbicidal amount of at least one substituted 1-amino-3-phenyluracil of the formula I as claimed in claim 1.

3. A composition for the desiccation and/or defoliation of plants, containing a desiccant and/or defoliant amount of at least one substituted 1-amino-3-phenyluracil of the formula I as claimed in claim 1, and at least one inert liquid and/or solid carrier and also, if desired, at least one adjuvant.

4. A process for controlling undesired plant growth, which comprises allowing a herbicidal amount of at least one substituted 1-amino-3-phenyluracil of the formula I as claimed in claim 1 to act on plants, their environment or on seeds.

5. A process for the desiccation and/or defoliation of plants, which comprises allowing a defoliant and/or desiccant amount of at least one substituted 1-amino-3-phenyluracil of the formula I as claimed in claim 1 to act on plants.

6. A process as claimed in claim 5, wherein cotton is treated.

* * * * *

UNITED STATES PATENT AND TRADEMARK OFFICE
CERTIFICATE OF CORRECTION

PATENT NO. : 5,700,805
DATED : December 23, 1997
INVENTOR(S) : SCHAEFER et al.

It is certified that error appears in the above-identified patent and that said Letters Patent is hereby corrected as shown below:

In the abstract, cover page item [57], line 25, "N-O-$CH_2$-CO-O=O-" should be
-- N-O-$CH_2$-CO-O- --.

In the abstract, cover page item [57], fourth line from the bottom, formula on the left. the bottom radical shown "$R^1$" should be --$R^2$-- and "$R^4$" should be --$R^5$--.

Column 21, claim 1, line 8, "alky)" should be --alkyl)--.

Signed and Sealed this

Seventeenth Day of March, 1998

*Attest:*

BRUCE LEHMAN

*Attesting Officer*  *Commissioner of Patents and Trademarks*